United States Patent
Yang et al.

(10) Patent No.: US 8,694,142 B2
(45) Date of Patent: Apr. 8, 2014

(54) DIRECT MANUFACTURING METHOD OF SELECTIVE LASER MELTING OF CUSTOMIZED TONGUE-SIDE ORTHODONTIC SUPPORT GROOVES

(75) Inventors: Yongqiang Yang, Guangzhou (CN); Shufan Wang, Guangzhou (CN)

(73) Assignee: South China University of Technology, Guangdong (CN)

( * ) Notice: Subject to any disclaimer, the term of this patent is extended or adjusted under 35 U.S.C. 154(b) by 212 days.

(21) Appl. No.: 12/918,692

(22) PCT Filed: May 19, 2008

(86) PCT No.: PCT/CN2008/000965
§ 371 (c)(1),
(2), (4) Date: Aug. 20, 2010

(87) PCT Pub. No.: WO2009/105922
PCT Pub. Date: Sep. 3, 2009

(65) Prior Publication Data
US 2010/0324715 A1    Dec. 23, 2010

(30) Foreign Application Priority Data
Feb. 27, 2008 (CN) .......................... 2008 1 0026491

(51) Int. Cl.
*G06F 19/00*    (2011.01)
(52) U.S. Cl.
USPC .................. 700/98; 700/97; 419/6; 433/9
(58) Field of Classification Search
USPC .................. 700/97, 98; 419/6; 433/9
See application file for complete search history.

(56) References Cited

U.S. PATENT DOCUMENTS

| | | | |
|---|---|---|---|
| 6,815,634 B2* | 11/2004 | Sonoda et al. | 219/121.63 |
| 7,780,907 B2* | 8/2010 | Schmidt et al. | 419/6 |
| 2002/0015654 A1* | 2/2002 | Das et al. | 419/8 |
| 2002/0020945 A1* | 2/2002 | Cho et al. | 264/460 |
| 2006/0222844 A1* | 10/2006 | Stinson | 428/323 |
| 2007/0015104 A1* | 1/2007 | Wiechmann et al. | 433/9 |
| 2008/0116118 A1* | 5/2008 | Zhu et al. | 209/142 |
| 2009/0266803 A1* | 10/2009 | Perret et al. | 219/121.85 |

OTHER PUBLICATIONS

Olaf Rehme ; Claus Emmelmann; Rapid manufacturing of lattice structures with selective laser melting. Proc. SPIE 6107, Laser-based Micropackaging, 61070K (Feb. 23, 2006); doi:10.1117/12.645848.*

* cited by examiner

*Primary Examiner* — Michael D Masinick
(74) *Attorney, Agent, or Firm* — MH2 Technology Law Group, LLP

(57) ABSTRACT

This invention has provided a direct manufacturing methodology of customized lingual orthodontic brackets by selective laser melting. The procedure is as follows. First of all, measure the dentition data and construct the 3D CAD model of the teeth through reverse engineering. Then a single soleplate of the lingual bracket contacting the tooth surface, as well as the ideal slot position is designed based on the teeth features. The designed models are later imported into the SLM machine and used to produce the brackets with desired materials directly. This method can actualize customized manufacture with highly accuracy, producing highly matched brackets all at once. The invention not only saves time and cost, but also has wide adaptation range and is able to adopt various raw materials. Different raw materials can be utilized in one step to accommodate specific capacity requirement of different parts of the brackets.

11 Claims, 3 Drawing Sheets

DIRECT MANUFACTURING METHOD OF SELECTIVE LASER MELTING OF CUSTOMIZED TONGUE-SIDE ORTHODONTIC SUPPORT GROOVES

CROSS-REFERENCE TO RELATED APPLICATIONS

This application is a U.S. National Stage application of PCT/CN2008/000965, filed 19 May 2008, the entire disclosure of which is hereby incorporated herein by reference.

FIELD OF THE INVENTION

This invention relates generally to the manufacturing of orthodontic brackets for straightening the teeth. More particularly, the invention relates to the methodology of direct manufacture of customized lingual orthodontic brackets by using selective laser melting.

BACKGROUND OF THE INVENTION

Orthodontics has been widely adapted in clinics to straighten or align teeth of a patient. The traditional method is to adhere brackets onto the teeth and run elastic wires through the bracket slots and provide the driving force, however, lingual orthodontics has been recognized and received wide interest since the 1970's. Lingual orthodontics involves bonding the bracket on the inner tooth surface instead of the labial tooth surface, which will not affect the appearance of the patient nor interfere with the closure of the lips. Meanwhile, the white stain caused by decalcification on the labial enamel of the tooth surface is avoided since the etching agent is not used. Also, it is easier for a doctor to observe the tooth position and shape from the lingual side during the treatment.

Currently, the brackets used for lingual orthodontics are off-the-shelf products which are manufactured as a single sized product. As such, the brackets have low adaptability for individual teeth. Because of the complicated appearance of the tooth lingual surface, smaller brackets are generally adapted for better adherence. The gap between the bracket and the teeth is filled up with dental adhesive. If there is more curvature on the tooth surface, more adhesive is needed, resulting in detachment of the bracket from the tooth surface. Comparing to labial orthodontics, lingual have more variable profile and require more matching brackets.

The major disadvantage of the lingual orthodontics is the stimulation of tongue. The tongue is one of the most sensitive organs in human body, which participates in frequent activities such as pronunciation and swallowing. Lingual brackets will deprive part of the room for the tongue and even cause pain by stimulating the edge of the tongue. In order to eliminate these side effects, manufacturing minute and fine lingual brackets has become the trend of development.

Rapid prototyping has been experimentally utilized in the manufacturing of lingual brackets. The general method is to firstly create a wax mold for the bracket through 3D-printing techniques, then fuse the mold and cast. There is no limitation for the brackets produced by this method and the individually customized manufacture is achievable. However, the process is intricate which involves multiple steps and long periods. Selective laser melting technique is an emerging and rapidly maturing prototyping technique and it has been utilized in the medical field. It can be used to directly manufacture lingual brackets which is usually composed of metal materials such as dental gold alloy or titanium alloys.

The existing manufacturing method of lingual brackets is standardized which can hardly satisfy the personal need of the patients, causing side effects on the treatment and resulting in heavy burden for the patients.

SUMMARY OF THE INVENTION

This invention can solve the problems occurring in the current manufacturing techniques of lingual orthodontic brackets as described above. It provides a direct manufacturing method of customized lingual brackets by utilizing selective laser melting. This method can not only produce customized product according to individual features, but also make more adhesive brackets on the teeth surface because of its high manufacturing accuracy.

This invention can be achieved by the methodology described below. The direct manufacturing methodology of customized lingual orthodontic brackets by selective laser melting includes the following procedures;

(1) Measure the dentition data of the teeth profile.

(2) Based on the dentition data, create a 3D CAD model of the patient's teeth through reverse engineering and save in computer.

(3) Design 3D CAD model for single lingual bracket structure, including the bottom plate in contact with teeth surface as well as the slots for the ideal position according to the orthodontia requirement, bracket material and tooth profile.

(4) Import the 3D CAD bracket structure model into the SLM machine and produce the brackets by laminated manufacturing directly.

(5) Modify the bracket surface based on clinical demand.

For better implementation of this invention, the dentition data measurement is achieved by CT scanner or non-contact 3D scanner or by conducting 3D scanning on a casted teeth model, with a scanning accuracy of less than 0.02 mm.

The teeth structure 3D CAD model described in step (2) is saved as .stl file.

The laminated manufacturing method described in step (4) is to use slicing software to separate the 3D CAD bracket structure model into thin layers and get the horizontal section model for each layer. Based on this section model, the SLM machine can directly produce metal brackets, ensuring the shape of each layer is consistent to the 3D CAD structure data.

The thickness of the layers described is 20 to about 50 um (micrometers) with the manufacturing accuracy of 5 to about 10 um by using between-layer additive error compensation method.

The thickness of the bracket bottom is less than 0.4 mm. The manufacturing material includes dental gold, titanium alloys, Co—Cr alloy and stainless steel powder, with the particle size less than 10 um.

The base of bracket is adhered to the tooth surface and the bracket slot is matched to the archwire. According to the requirement of mechanical properties, different alloys or composition of powder is required for the layers during the selective laser melting manufacturing process. After they are built up, the brackets will have a gradient and better performance.

During the SLM process, the brackets are prepared in a sealed chamber filled with inert gas, ensuring high quality of the products.

Fiber laser is utilized for the selective laser melting. The laser has continuous output power of 100-200 W and the light beam quality factor of $M^2<1.1$, with the focused spot diameter less than 25 um.

This invention has the following advantages and effects comparing to the existing technology.

1. Customization. The methodology provided by this invention is off the limit of the product complexity. Therefore, the soleplate of the bracket, which holds or connects the bracket to the tooth surface, is designed specifically according to the tooth surface profile, instead of the generalized gridding pattern. The customized brackets can meet individual demand. The slot on the bracket has high accuracy and low thickness, and the base of the bracket has different height because of the selected material, which can highly match the tooth surface and maximize the contact surface. Also, because each slot has its own position and shape to cooperate with the archwire, the twisting error is minimized and optimal orthodontic result can be actualized.

2. Short manufacturing period. Using selective laser melting technique can turn the designed model into metal product rapidly. The bracket manufacturing involves only one step, saving time and cost.

3. Wide adaptation range. This invention can be used to manufacture brackets from dental gold, stainless steel, Ti alloy and Co—Cr alloy.

4. Different materials can be used in the same process to meet the different capability requirements.

DETAILED DESCRIPTION

The practice example and figures help to illustrate this invention in details. However, the implement method of this invention can vary according to need.

Figure 1:
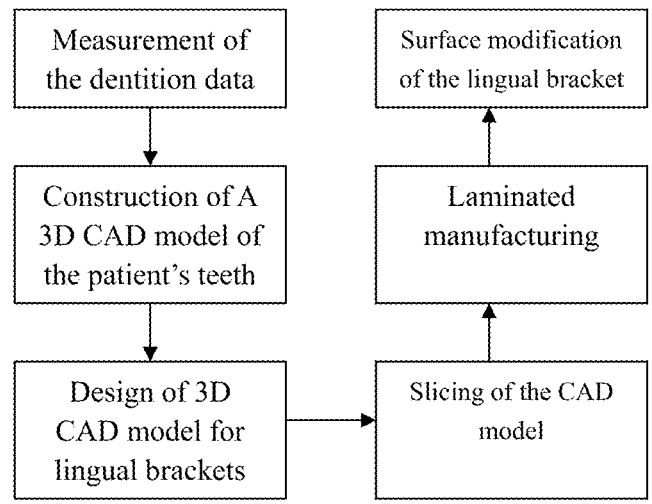
FIG. 1 is the technical flowchart of the direct manufacturing methodology of the lingual orthodontic brackets by selective laser melting.
Figure 2:
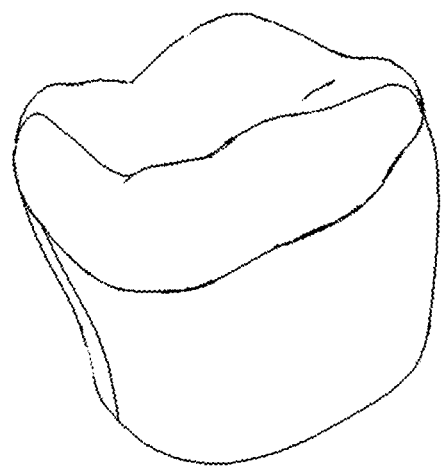
FIG. 2 is the 3D CAD model of a constant tooth created on the dentition data.

As shown in FIG. 1, the flowchart of the direct manufacturing methodology of the lingual orthodontic brackets by selective laser melting is as follows.

(1) Measure dentition data and analyze the parameter of the tooth profile. The measurement uses CT layer scanning or non-contact 3D scanner directly on the patient's teeth, or use 3D readings on the teeth model previously casted. The scanning accuracy described above is less than 0.02 mm.

(2) Based on the given dentition data, construct the 3D CAD model using the reverse engineering method and save in the computer as .stl files. The outside structure of teeth is complicated, usually as irregular curves.

Figure 3:
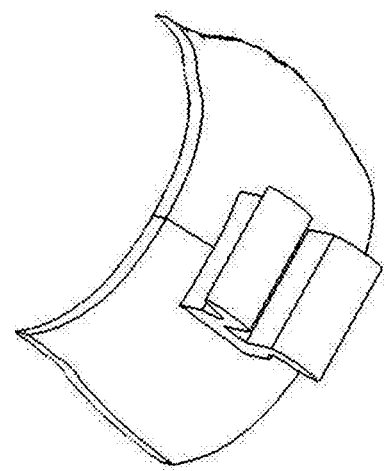
FIG. 3 is the 3D CAD model of a bracket designed based on the tooth structure showed in FIG. 2.
Figure 4:
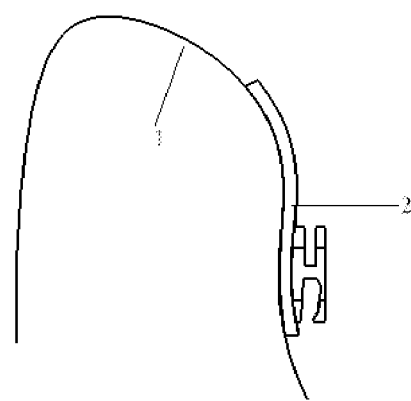
FIG. 4 is the 3D CAD model of a bracket designed from a single front tooth structure.

(3) As shown in FIG. 3, 3D CAD structure models of lingual brackets are designed by computer according to the orthodontic requirements, material and teeth profile. The bracket model design includes the soleplate contacting with the tooth surface as well as the slot located on its ideal position. FIG. 4 is the curve on tooth surface and the designed bracket, the bottom of bracket or soleplate 2 is completely matched to the lingual surface of tooth 1.

(4) Import the designed model from step 3 into the SLM machine and produce the bracket layer by layer. Slicing software is used to separate the 3D CAD structure model and the 2D model of each section is acquired. The thickness of the layers is 20 to about 50 um with the manufacturing accuracy of 5 to about 10 um by using between-layer additive error compensation method. Based on this section model, the SLM machine can directly produce metal brackets, ensuring the shape of each layer is consistent to the 3D CAD structure data.

Figure 5:
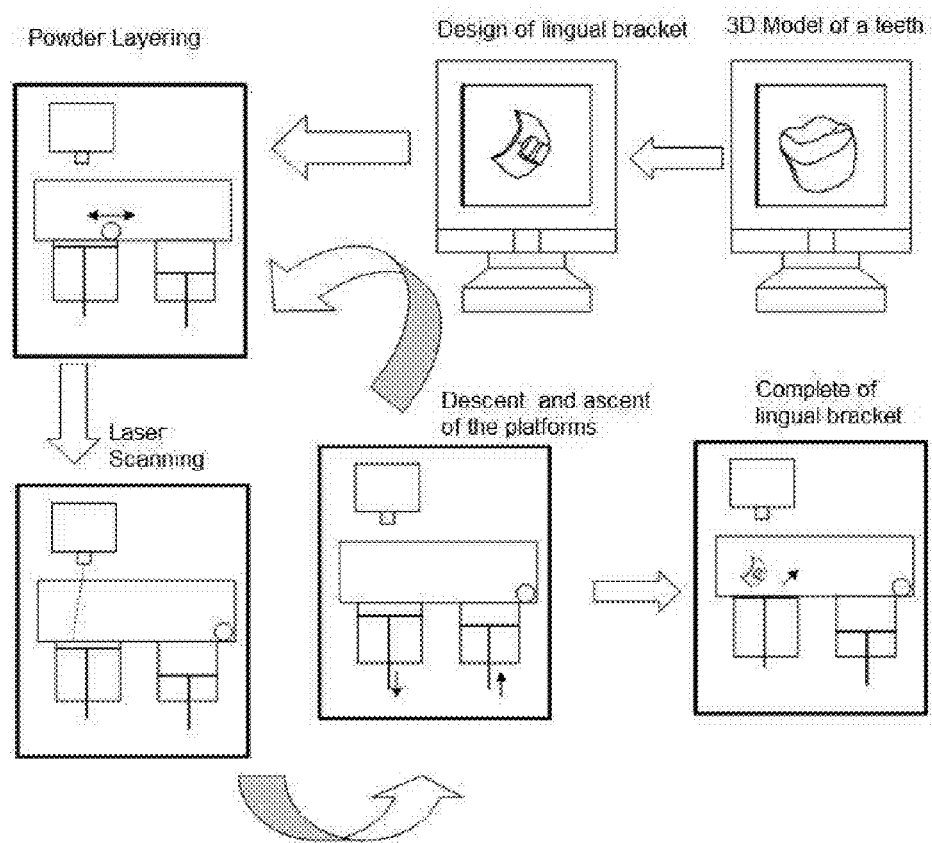
FIG. 5 is the technical sketch map of the layering manufacturing methodology of the lingual orthodontic brackets by selective laser melting.

As shown in FIG. 5, the procedure for the layering manufacturing methodology of the lingual orthodontic brackets by selective laser melting is as follows.

Firstly, the 3D CAD model of the teeth is constructed from the reverse engineering measurement data. Based on this model, single lingual bracket 3D CAD models are designed according to the orthodontic requirement, material and teeth profile. Then, the model can be imported into the SLM machine and it can directly manufacture the bracket layer by layer. The molding process involves three steps: 1, spread the powder homogenously on the platform of the molding compartment; 2, scan by the laser beam controlled by computer; 3, descend the plunger of the molding compartment by one layer distance and raise the plunger of the material compartment by one layer thickness; repeat these three steps until finished. During the SLM process, the brackets are prepared in a sealed chamber filled with inert gas. Finally, bracket products are taken out from the chamber.

Fiber laser is utilized for the selective laser melting. The laser has continuous output power of 100-200 W and the light beam quality factor of $M^2<1.1$, with the focused light spot diameter less than 25 um.

The soleplate of the bracket is less than 0.4 mm thick. The raw materials of the brackets include powder of dental gold, stainless steel, Ti alloy and Co—Cr alloy. The powder size is less than 10 um.

The base of bracket is adhered to the tooth surface and the bracket slot is matched to the archwire. According to requirements of mechanical properties, different alloys or composition of powder is required for the layers during the selective laser melting manufacturing process. After built up, the brackets will have a gradient and better performance.

(5) Process the bracket surface based on clinical demand.

Better implementation of this invention can be achieved by the description above. The previous example is only a well conducted case of this invention, but not a limitation of its implementation. Equal changes and modification made based on the content of this invention is covered in the protection range of the patent.

The invention claimed is:

1. A method of manufacturing customized lingual orthodontic brackets by selective laser melting, said method comprising:

(1) measuring dentition data of a profile of teeth of a patient, wherein measuring dentition data is performed using a CT scanner;

(2) based on the dentition data, creating a three dimensional computer assisted design (3D CAD) model of the patient's teeth using reverse engineering, and saving the 3D CAD model on a computer;

(3) designing a 3D CAD model for a single lingual bracket structure, wherein the model includes at least a) the bottom plate in contact with a particular tooth's surfaces, b) slots for ideal positioning according to the orthodontia needs of the patient, c) a bracket material, and d) the particular tooth's profile;

(4) importing the 3D CAD bracket structure model into a Selective Laser Melting (SLM) machine, wherein the SLM machine comprises a molding compartment and a material compartment, and the molding compartment comprises a platform and a plunger, and directly producing the bracket by layer manufacturing, wherein the bracket is produced in a sealed chamber filled with inert gas and wherein a fiber laser is used for selective laser melting, wherein producing the bracket by layer manufacturing comprises using slicing software to separate the 3D CAD bracket structure model into layers and to get a horizontal section model for each layer to ensure that the shape of each layer produced by the SLM machine is consistent with the 3D CAD structure data, wherein directly producing the bracket by layer manufacturing further comprises a) spreading a powder on the platform of the molding compartment; b) scanning the powder with the fiber laser; c) descending the plunger of the molding compartment by one layer distance and raising the plunger of the material compartment by one layer distance; d) repeating steps a)-c); and e) removing the bracket from the SLM machine; and wherein each layer produced by the SLM machine comprises a different alloy or composition of powder, such that the bracket has a gradient; and (5) processing the bracket surface based on clinical demand.

2. The method according to claim 1, wherein scanning accuracy is less than 0.02 mm.

3. The method according to claim 1, wherein the 3D CAD model is saved as an .stl file.

4. The method according to claim 1, wherein the thickness of the manufactured layers is from 20 to about 50 micrometers (um).

5. The method according to claim 4, wherein the bracket is less than 0.4 mm thick.

6. The method according to claim 5, wherein the manufactured layers of the bracket comprise a material selected from the group consisting of dental gold, titanium alloy, Co—Cr alloy, and stainless steel powder, having a particle size of less than 10 um.

7. The method of claim 4, wherein the manufacturing accuracy is from 5 to about 10 um, and wherein the accuracy is achieved by using a between layer additive error compensation method.

8. The method according to claim 1, wherein selection of the material for producing layers of the bracket is based on different force demands.

9. The method of claim 1, wherein the laser has continuous output power of 100-200 W and a light beam quality factor of $M^2 < 1.1$, with a focused light spot diameter less than 25 um.

10. The method of claim 1, wherein measuring dentition data is performed by conducting 3D scanning on a casted teeth model.

11. The method of claim 1, wherein the powder is selected from the group consisting of dental gold, titanium alloy, Co—Cr alloy, and stainless steel powder, having a particle size of less than 10 um.

* * * * *